US011148130B2

(12) United States Patent
Procyshyn et al.

(10) Patent No.: US 11,148,130 B2
(45) Date of Patent: Oct. 19, 2021

(54) METHOD FOR PROTECTING AND UNPROTECTING THE FLUID PATH IN A CONTROLLED ENVIRONMENT ENCLOSURE

(71) Applicant: VANRX PHARMASYSTEMS INC., Burnaby (CA)

(72) Inventors: Christopher A. Procyshyn, Surrey (CA); Jeroen Immerzeel, Squamish (CA); Steve Sang Joon Park, Toronto (CA); Ross M Gold, North Vancouver (CA)

(73) Assignee: V ANRX PHARMASYSTEMS INC., Burnaby (CA)

( * ) Notice: Subject to any disclaimer, the term of this patent is extended or adjusted under 35 U.S.C. 154(b) by 0 days.

(21) Appl. No.: 16/799,767

(22) Filed: Feb. 24, 2020

(65) Prior Publication Data

US 2020/0215527 A1     Jul. 9, 2020

Related U.S. Application Data

(62) Division of application No. 15/898,641, filed on Feb. 18, 2018, now Pat. No. 10,688,484, which is a
(Continued)

(51) Int. Cl.
*B01L 1/02* (2006.01)
*C12M 1/00* (2006.01)
(Continued)

(52) U.S. Cl.
CPC ............... *B01L 1/025* (2013.01); *A61L 2/07* (2013.01); *A61L 2/16* (2013.01); *A61L 2/24* (2013.01);
(Continued)

(58) Field of Classification Search
CPC ............. B01L 1/025; B01L 2300/0832; B01L 2200/0689; B01L 2200/141; C12M 29/00;
(Continued)

(56) References Cited

U.S. PATENT DOCUMENTS 4,376,634 A    3/1983  Prior et al.
4,976,699 A   12/1990  Gold
(Continued)

FOREIGN PATENT DOCUMENTS

WO    9633806 A1    10/1996
WO    0818904 A2     2/2008
(Continued)

OTHER PUBLICATIONS

Federal Institute of Industrial Property (Rospatent); PCT International Preliminary Report on Patentability for PCT/US2012/047765, dated Jan. 28, 2014; PCT International Search Report for PCT/US2012/47765.
(Continued)

*Primary Examiner* — Timothy C Cleveland
(74) *Attorney, Agent, or Firm* — Kevin R. Erdman; Brannon Sowers & Cracraft PC (57) ABSTRACT

A controlled environment enclosure comprises a robotic arm manipulation system used to protect and unprotect a fluid path within the controlled environment enclosure. The apparatus allows the fluid path to be protected against dangerous decontamination vapors and chemicals before the controlled environment enclosure is decontaminated, the method not requiring the use of gloves or other means that degrade the integrity of the controlled environment enclosure. The apparatus similarly allows the fluid path to be unprotected for use without the use of gloves, the method not requiring the use of gloves or other means that degrade the integrity of the controlled environment enclosure when decontaminated is
(Continued)

completed. The apparatus and method allow for the protecting, unprotecting and decontaminating sequences to be automated.

38 Claims, 8 Drawing Sheets

Related U.S. Application Data division of application No. 14/890,223, filed as application No. PCT/US2012/047765 on Jul. 20, 2012, now Pat. No. 9,993,815.

(60) Provisional application No. 61/510,780, filed on Jul. 22, 2011.

(51) Int. Cl.
    *C12M 1/12*     (2006.01)
    *B25J 21/00*     (2006.01)
    *A61L 2/07*     (2006.01)
    *A61L 2/16*     (2006.01)
    *A61L 2/24*     (2006.01)
    *G01N 35/00*     (2006.01)

(52) U.S. Cl.
    CPC .............. *B25J 21/00* (2013.01); *C12M 29/00* (2013.01); *C12M 37/02* (2013.01); *C12M 41/14* (2013.01); *B01L 2200/0689* (2013.01); *B01L 2200/141* (2013.01); *B01L 2300/0832* (2013.01); *G01N 35/0099* (2013.01); *G01N 2035/00277* (2013.01)

(58) Field of Classification Search
    CPC ......... C12M 37/02; C12M 41/14; A61L 2/07; A61L 2/16; A61L 2/24; B25J 21/00; G01N 2035/00277; G01N 35/0099
    See application file for complete search history.

(56) References Cited

U.S. PATENT DOCUMENTS

| | | |
|---|---|---|
| 5,021,049 A | 6/1991 | Howard |
| 5,341,854 A | 8/1994 | Zezulka et al. |
| 5,769,224 A | 6/1998 | Poncy |
| 6,116,670 A | 9/2000 | Palone |
| 6,203,535 B1 | 3/2001 | Barney |
| 6,409,701 B1 | 6/2002 | Cohn |
| 8,372,353 B2 | 2/2013 | Lee et al. |
| 2006/0136095 A1 | 6/2006 | Rob |
| 2009/0221059 A1 | 9/2009 | Williams et al. |
| 2009/0298129 A1 | 12/2009 | Spence |
| 2010/0288060 A1 | 11/2010 | Ronsick |
| 2016/0052683 A1 | 2/2016 | Christensen |

FOREIGN PATENT DOCUMENTS

| | | |
|---|---|---|
| WO | 09123911 A1 | 10/2009 |
| WO | 101457474 A1 | 5/2010 |
| WO | 2013016248 A1 | 1/2013 |
| WO | 2014161831 A2 | 9/2014 |
| WO | 2015023924 A2 | 2/2015 |
| WO | 2015153623 A1 | 10/2015 |

OTHER PUBLICATIONS

Korean Patent Office (KIPO) Notice of Preliminary Rejection, Korean Patent Application No. 10-2014-7004709.
Federal Institute of Industrial Property (Rospatent); PCT Written Opinion of The International Searching Authority for PCT/US2012/047765, dated Oct. 31, 2012.
Federal Institute of Industrial Property (Rospatent); PCT International Search Report of The International Searching Authority for PCT/US2012/047765, dated Nov. 22, 2012.
European Patent Office; Supplementary European Search Report in corresponding EPO application 12818292.0 regional stage of PCT/US2012/047765 with amended Claims and response.
International Search Report by International Searching Authority (International Application No. PCT/IB2016/001958), dated May 19, 2017.
Written Opinion by International Searching Authority (International Application No. PCT/IB2016/001958), dated May 19, 2017.

PRIOR ART

METHOD FOR PROTECTING AND UNPROTECTING THE FLUID PATH IN A CONTROLLED ENVIRONMENT ENCLOSURE

CROSS-REFERENCE TO RELATED APPLICATIONS

The present application is a Divisional of U.S. patent application Ser. No. 15/898,641, filed Feb. 18, 2018, now U.S. Pat. No. 10,688,484, issued Jun. 30, 2020; which is a Divisional of U.S. patent application Ser. No. 14/890,223, filed Jul. 27, 2016, now U.S. Pat. No. 9,993,815, issued Dec. 1, 2016; which claims priority under 35 U.S.C § 371 of PCT Patent Application Number PCT/US2012/047765, filed Jul. 20, 2012, which claims priority under 35 U.S.C § 119(e) of U.S. Patent Provisional Application Ser. No. 61/510,780, filed Jul. 22, 2011, the disclosures of which are incorporated by reference herein.

BACKGROUND OF THE INVENTION

Field of the Invention

This document relates generally to controlled environment enclosures and in particularly to a method for protecting and unprotecting the fluid path in a controlled environment enclosure.

Description of the Related Art

Controlled environment enclosures are known in the art. Such enclosures are used, for example, for containment of hazardous materials. In other examples, controlled environment enclosures are used to provide controlled environments with limited numbers of particulates.

In the art, controlled environment enclosures are typically fitted with ports for transfer of materials in and out of the enclosure and the ports are fitted with gloves for manual manipulation of equipment, parts or materials inside the enclosure. Such gloves are subject to significant risk of puncture.

In some examples known in the art the controlled environment enclosure is also used to limit exposure to viable particulates. Such controlled environment enclosures may be required for aseptic processing of cell cultures and for the manufacture of pharmaceutical products, medical devices, food or food ingredients. In these cases it is a requirement that the controlled environment enclosure be decontaminated. This may be done thermally using steam or chemically using chemical agents. Suitable chemical agents known in the art include hydrogen peroxide, ozone, beta-propiolactone, aziridine, formaldehyde, chlorine dioxide, ethylene oxide, propylene oxide, and peracetic acid. In most cases the decontamination and sterilization operations have to be preceded by a cleaning process. Such cleaning processes have the function of removing major contamination by simple mechanical and chemical action.

In some examples in the prior art the controlled environment also contains automated equipment. Such automated equipment includes machines for filling of vials. The automated equipment located in the controlled environment is typically of such a size and complexity that it cannot be operated fully automatically without human intervention. Such human intervention typically requires the use of gloves with the associated risk of puncture.

Fluid paths within the controlled environment enclosures may be made from flexible tubing materials and can therefore have significant gas permeability. Gases that naturally occur in air, such as oxygen and carbon dioxide, as well as chemical decontamination agents, are known to diffuse into these tubing materials. Accumulation of these agents in flexible tubing and subsequent delayed release can be a major contamination problem during operation. This applies in particular to products or solutions that are sensitive to exposure to alkylating agents, oxidizers, radicals or carbon dioxide. A typical example of human intervention involving the use of gloves is the installation of the fluid path or multiple fluid paths after the completion of decontamination.

In view of the above there remains a need for controlled environments that do not require human intervention via the use of gloves.

SUMMARY

In one aspect of the invention there is provided a method for installing a fluid path within a controlled environment enclosure comprising, protecting the fluid path against an environment external to the fluid path; introducing the fluid path into the controlled environment enclosure; decontaminating the controlled environment enclosure; and mechanically unprotecting the fluid path within the controlled environment enclosure. The mechanically unprotecting can be by a robotic arm manipulation system. The decontaminating the controlled environment enclosure is automatically done after the introducing the fluid path into the controlled environment enclosure. The unprotecting is automatically done after the decontaminating the controlled environment enclosure.

In one aspect of the invention there is provided a method for transferring within a controlled environment enclosure a fluid along a fluid path to a destination within the controlled environment enclosure, comprising protecting the fluid path against an environment external to the fluid path; introducing the fluid path into the controlled environment enclosure; decontaminating the controlled environment enclosure; mechanically unprotecting the fluid path within the controlled environment enclosure; and transferring the fluid to the destination along the fluid path. The mechanically unprotecting can be by a robotic arm manipulation system. The fluid path can comprise a pre-sterilized tube. The method can further comprise filtering the fluid in the fluid path and the filtering can be sterile filtering. The destination can be at least one of a culture of cells, a culture of tissue, an enzyme solution, a suspension of immobilized enzymes, a mix of active ingredients, and an excipient. The fluid can be an aseptic fluid. The controlled environment enclosure can be an isolator. The destination can be microwell plates or containers for pharmaceutical products.

In one aspect of the invention there is provided a method for uninstalling a fluid path from a controlled environment enclosure, comprising mechanically protecting the fluid path within the controlled environment enclosure; decontaminating the controlled environment enclosure; opening the controlled environment enclosure; and removing the fluid path from the controlled environment enclosure. The mechanically protecting can be by a robotic arm manipulation system. The decontaminating the controlled environment enclosure can be done automatically after the protecting the fluid path. The opening the controlled environment enclosure can be done automatically after the decontaminating the controlled environment enclosure.

In one aspect of the invention there is provided a method for decontaminating a controlled environment enclosure having a fluid path, the method comprising mechanically protecting by a robotic action the fluid path within the controlled environment enclosure; decontaminating the controlled environment enclosure; and opening and closing the controlled environment enclosure. The opening and closing the controlled environment enclosure can be done before or after the decontaminating the controlled environment enclosure. The mechanically protecting can be by a robotic arm manipulation system. The decontaminating the controlled environment enclosure can be done automatically after the mechanically protecting the fluid path.

The inventors envision that compact and well-designed automated equipment can be operated inside closed controlled environments without the use of any gloves, eliminating thereby the risk of leaky gloves. The invention provides a method of installing a fluid path inside a controlled environment enclosure without the use of gloves. This requires the fluid path to be protected during the decontamination process and to be unprotected prior to the use of the fluid path. Furthermore, the fluid path can be automatically closed after use.

The closed fluid path can be re-opened and re-used at a later time. This can be useful for continuing the use of the fluid path after unplanned events that require breaking of the integrity of the enclosed controlled environment. Additionally, the closing of the fluid path can be particularly useful in situations where the fluid path has been in use for transfer of hazardous substances. After closing of the fluid path, the enclosed environment can be cleaned and decontaminated; after which the fluid path can be removed.

Other features, elements, steps, characteristics and advantages of the present invention will become more apparent from the following detailed description of preferred embodiments of the present invention.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
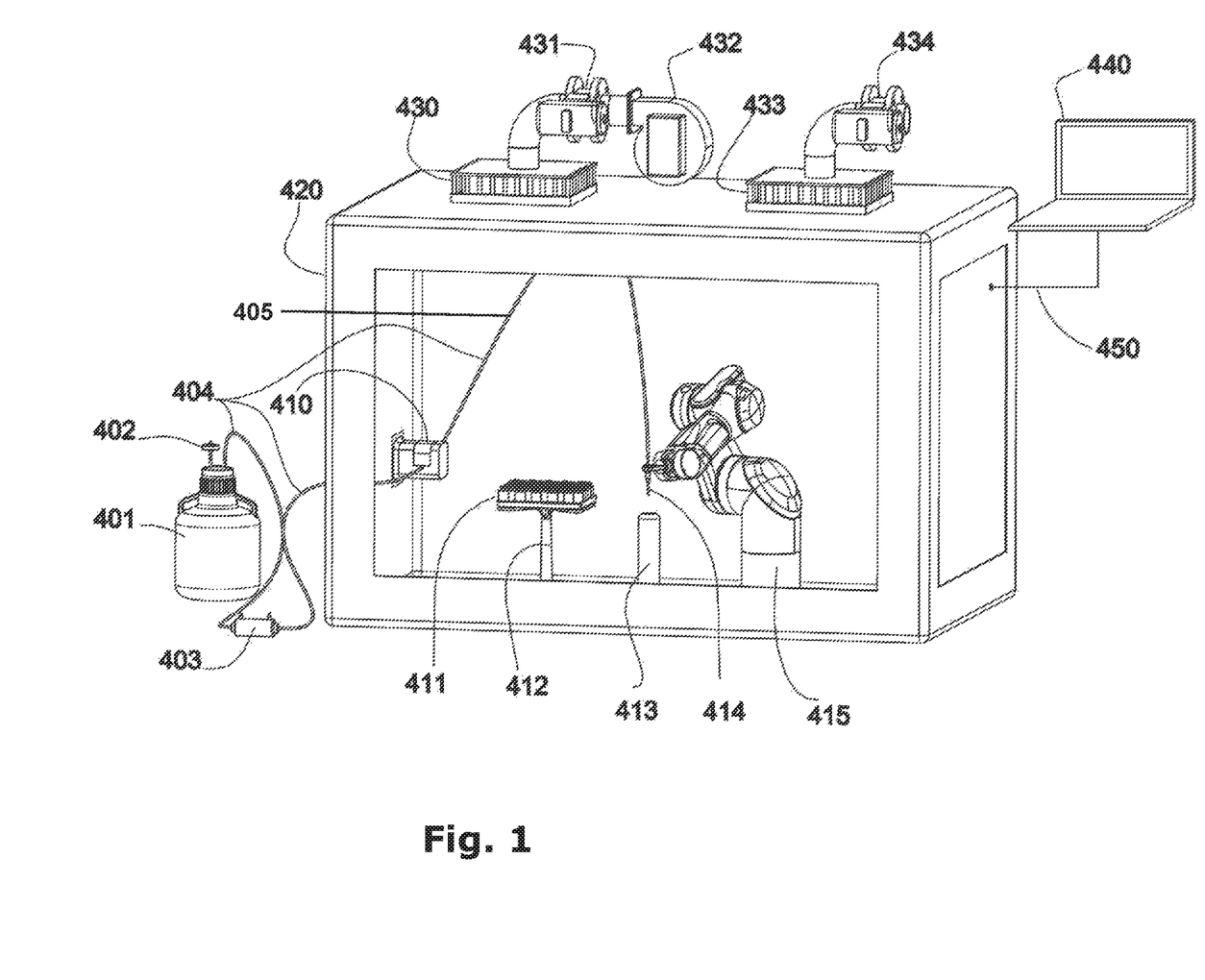
FIG. 1 shows an apparatus for the protecting and unprotecting of a fluid path in a controlled environment enclosure.

FIG. 1 shows an embodiment of an apparatus for protecting and unprotecting of a fluid path 404 in a controlled environment enclosure 420. The term "fluid" as used herein denotes any liquid, gas, liquid-gas mixtures and any mixture of solids in liquid that has fluid attributes, such as flowability or having appreciable fluidity at ambient temperature and pressure, including, without limitation, a dispersion of a solid or solids in a liquid, an emulsion, a slurry, a microemulsion, colloidal suspension, a suspension, a suspension of liposomes, a suspension of micelles or the like. The term "fluid path" as used herein denotes any single channel or multi channel tubing, rigid or flexible, for transporting a fluid.

A fluid path 404 starts at a container 401. The term "container" as used herein denotes any vessel suitable to hold a fluid, including without limitation any vial, syringe, ampoule, carpule, bottle, flask, beaker, bag, well in microwell plates, well in multi-well plates, or tube. The container 401 is fitted with an air filter 402. The container 401 can be equipped with optional sensors (not shown) to measure volume, weight of fluid, or other parameters. In some embodiments there can be multiple containers connected in parallel or in series with one another. Along the fluid path 404 there can be optional measuring devices (not shown) that measure properties, including without limitation any one or more of pressure, flow, temperature, density and conductivity. The fluid path 404 can be fitted with a filter element 403. The filter element 403 can be selected to be suitable for sterile filtration of fluids.

The fluid path 404 enters the controlled environment enclosure 420 at an opening (not apparent in FIG. 1). In FIG. 1 the fluid path 404 consists of flexible tubing 405. The opening is sealed. The sealing can be, for example, via the use of a suitable flange (not shown). The container 401 and air filter 402 can be located outside the controlled environment enclosure 420, as shown in FIG. 1. In other embodiments of the invention the container 401 and air filter 402 can be located inside the controlled environment enclosure 420.

Controlled environment enclosure 420 is equipped with an inlet filter 430, an inlet valve 431, a blower 432, an outlet filter 433 and an outlet valve 434. The characteristics of blower 432, inlet filter 430 and outlet filter 433 are chosen to yield a controlled environment inside controlled environment enclosure 420. As understood by those skilled in the art, various other filter and blower arrangements are possible to establish a controlled environment inside controlled environment enclosure 420. A suitable controlled environment can be obtained, for example without limitation, by means of any one or more of turbulent airflow, horizontal unidirectional airflow and vertical unidirectional airflow.

The fluid from container 401 can be transferred through the fluid path 404 by a number of different mechanisms, including without limitation a peristaltic pump 410 as shown in FIG. 1, a difference in pressure between the container 401 and the controlled environment enclosure 420, a difference in static height of the container 401 and the end of the fluid path 404, a gear pump, a lobe pump, a membrane pump, a piston pump, or a syringe pump.

The flexible tubing 405 of the fluid path 404 can terminate with an end piece 414. A suitable end piece can be, for example without limitation, a fill needle, a pipette dispensing system, a syringe dispensing system, a valve dispensing system, quick connectors, aseptic connectors, dispense tips and a needle for piercing of elastomers. In FIG. 1 the end piece 414 is selected to be a fill needle.

The end piece 414 can be manipulated inside the controlled environment enclosure 420 by mechanical means, for example, a robotic arm manipulation system 415. Suitable robotic arm manipulation systems for mechanically manipulating end piece 414 include, but are not limited to, 6-axis robotic arms, Selective Compliant Articulated Robot Arm (SCARA) systems, r-theta robots, or combinations of linear actuators and rotary actuators.

Fluids are transferred along the fluid path 404 to a destination, which can be containers such as the tray with vials 411 located on pedestal 412 in FIG. 1. The fluid path 404 may be employed for a variety of purposes including without limitation the filling of empty containers, washing and rinsing of containers, adding fluid to containers with a freeze dried powder, adding fluids to containers containing excipients and/or active ingredients, adding medium to cells, tissue or microbes, inoculating cells or microbes, adding substrate to enzyme solutions or suspensions of immobilized enzymes, adding gases such as argon or nitrogen to create an inert head space in containers, adding gases such as nitrogen, air or carbon dioxide to cells and removing fluids out of containers by suction. The term "excipient" as used herein denotes an inert substance used as a diluent or vehicle for a drug.

Fluid path 404 may in some applications be required for aseptic transfer of fluids. In such a case fluid path 404 can be pre-sterilized before installation in the controlled environment enclosure 420. The aseptic part of the fluid path 404 can start with container 401 or with filter 403. Installation of the aseptic fluid path 404 requires sealing of the end piece 414.

Figure 4:
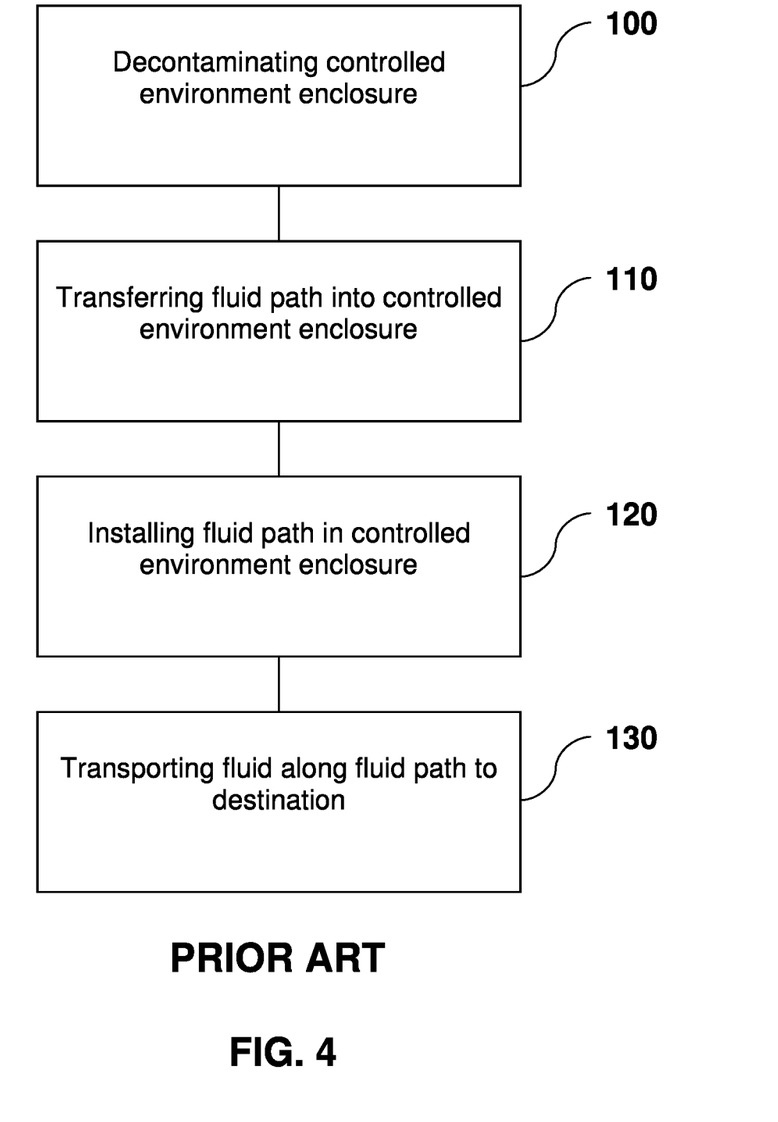
FIG. 4 is a flow chart for the typical prior art method.

FIG. 4 is a flowchart showing the prior art method for installing a fluid path in a prior art controlled environment enclosure. The prior art method requires the steps in sequence of decontaminating (100) the prior art controlled environment enclosure; transferring (110) the fluid path into the prior art controlled environment enclosure; and installing (120) by hand the fluid path in the prior art controlled environment enclosure, before using (130) the fluid path for the purpose for which it is intended.

Figure 5:
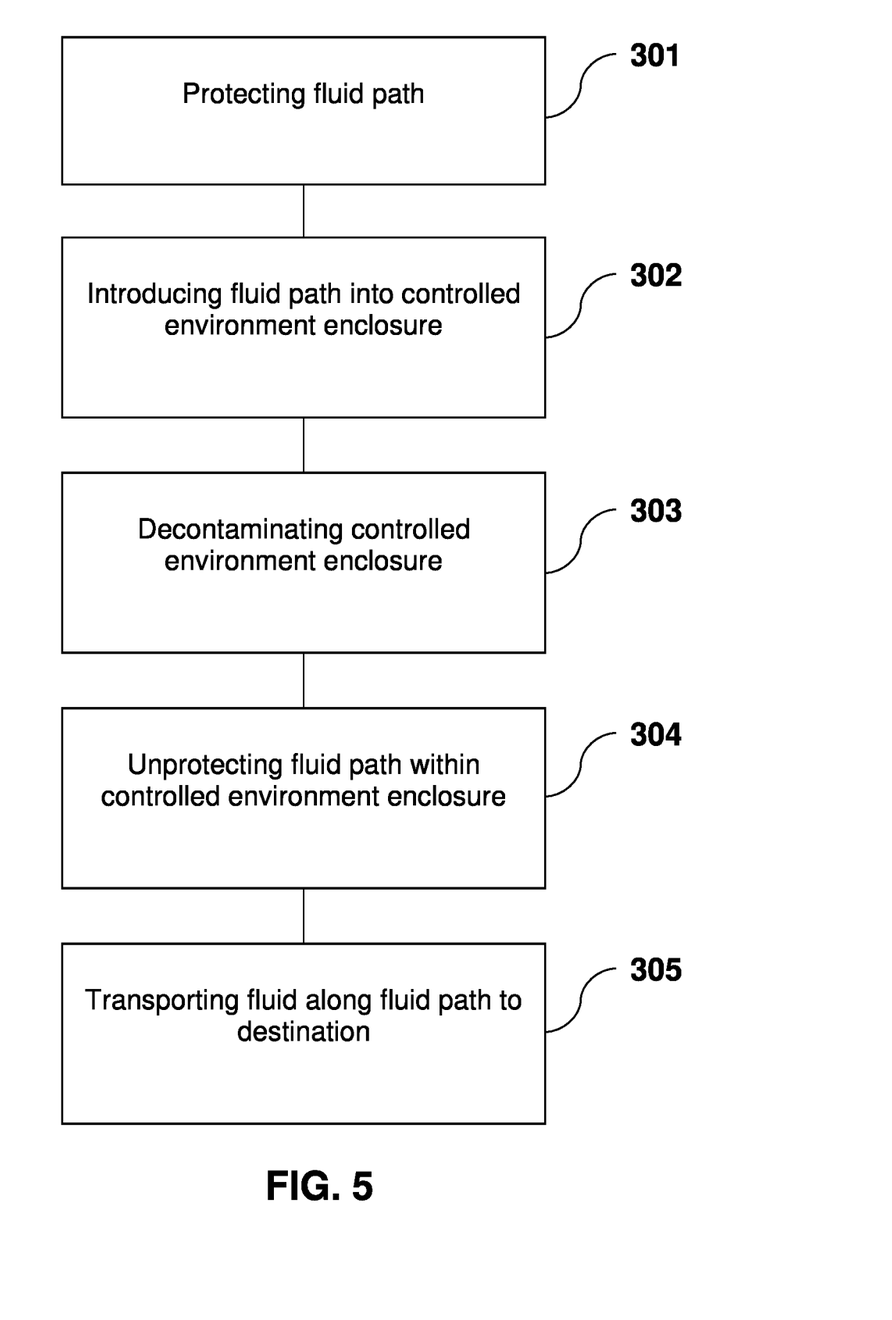
FIG. 5 shows a method flow chart of an aspect of the invention

In an aspect of the invention there is provided a method for installing a fluid path 404 in the controlled environment enclosure 420. Referring to the apparatus of FIG. 4 and the flow chart of FIG. 5, the method comprises protecting (301) the fluid path 404 against an environment external to the fluid path 404, introducing (302) the fluid path 404 into the controlled environment enclosure 420, decontaminating (303) the controlled environment enclosure 420, and mechanically unprotecting (304) the fluid path 404. In its unprotected state fluid path 404 can then be used for transporting (305) fluids to destination 411, which fluids can be aseptic or sterile fluids. Such transporting (305) of fluids can comprise filtering the fluid in the fluid path 404 using filter element 403 and the filtering can be sterile filtering. The terms "sterile" and "aseptic" are used interchangeably in this specification. The term "decontamination" as used herein denotes a process for removing or inactivating contamination, including without limitation viruses, bacteria, spores, prions, molds, yeasts, proteins, pyrogens and endotoxins, to acceptable levels. "Decontamination" as used herein includes both sterilization (that is, the destruction of all microorganisms, including bacterial spores to a probability of surviving organisms of typically less than $1:10^6$) and disinfection (that is, the destruction and removal of specific types of micro-organisms).

Figure 2:
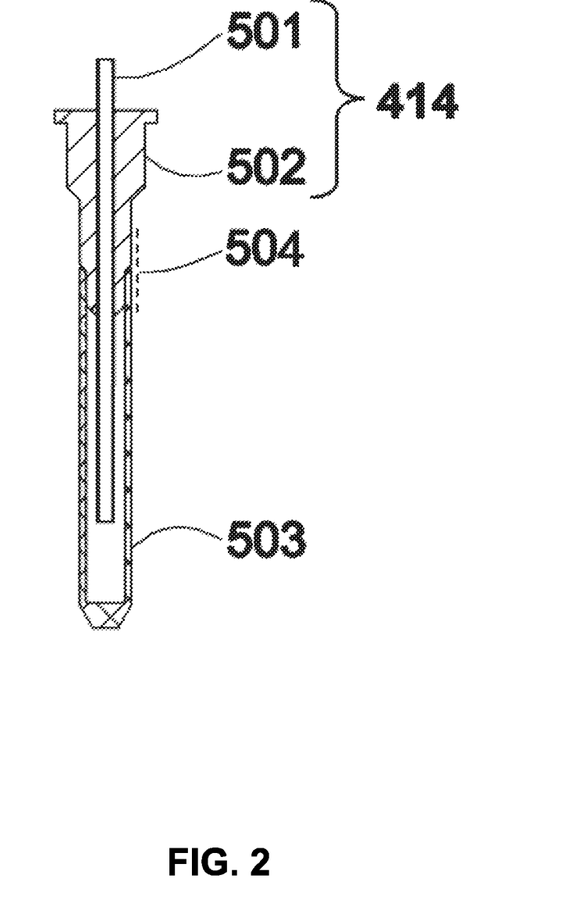
FIG. 2 shows detail of an end piece of an apparatus for the protecting and unprotecting of a fluid path in a controlled environment enclosure.

In FIG. 2 a suitable arrangement for mechanically unprotecting (304) fluid path 404 is shown, comprising end piece 414 of fluid path 404 in the form of a fill needle, together with a fill needle sheath 503. The fill needle 414 comprises fill needle tubing 501 and fill needle hub 502. When the fluid path 404 is within controlled environment enclosure 420, the fill needle sheath 503 can be stored in a sheath removal station 413 of the controlled environment enclosure 420 shown in FIG. 1.

The fill needle hub 502 and the fill needle tubing 501 can be glued or welded together. In alternative embodiments the fill needle hub 502 and the fill needle tubing 501 can be made as one part out of solid material. The fill needle sheath 503 can be manufactured using materials with different thermal expansion coefficients to allow it to slide on and off the fill needle hub 502 after thermal expansion. Alternatively, the needle sheath 503 can be designed to have a sliding fit on the fill needle hub 502 using porous PTFE or a steam permeable elastomeric material.

Protecting (301) the fluid path 404 comprises sealingly placing the fill needle sheath 503 over the fill needle 414 such that the fill needle sheath 503 seals with the needle hub 502. The fill needle sheath 503 and needle hub 502 can be equipped with one or multiple tamper evident features 504 that will provide evidence of breaking the seal between needle hub 502 and fill needle sheath 503. Possible tamper evident features include but are not limited to heat shrink bands, tape seals, breakable ring, tear-off connectors and snap connect tear-off connectors. Correspondingly, unprotecting (304) the fluid path 404 comprises removing the fill needle sheath 503 from the fill needle 414, thereby exposing the fill needle 414 to an environment within the controlled environment enclosure 420. When the fill needle 414 is in use within the controlled environment enclosure 420, the fill needle sheath 503 is stored in the sheath removal station 413.

Figure 3:
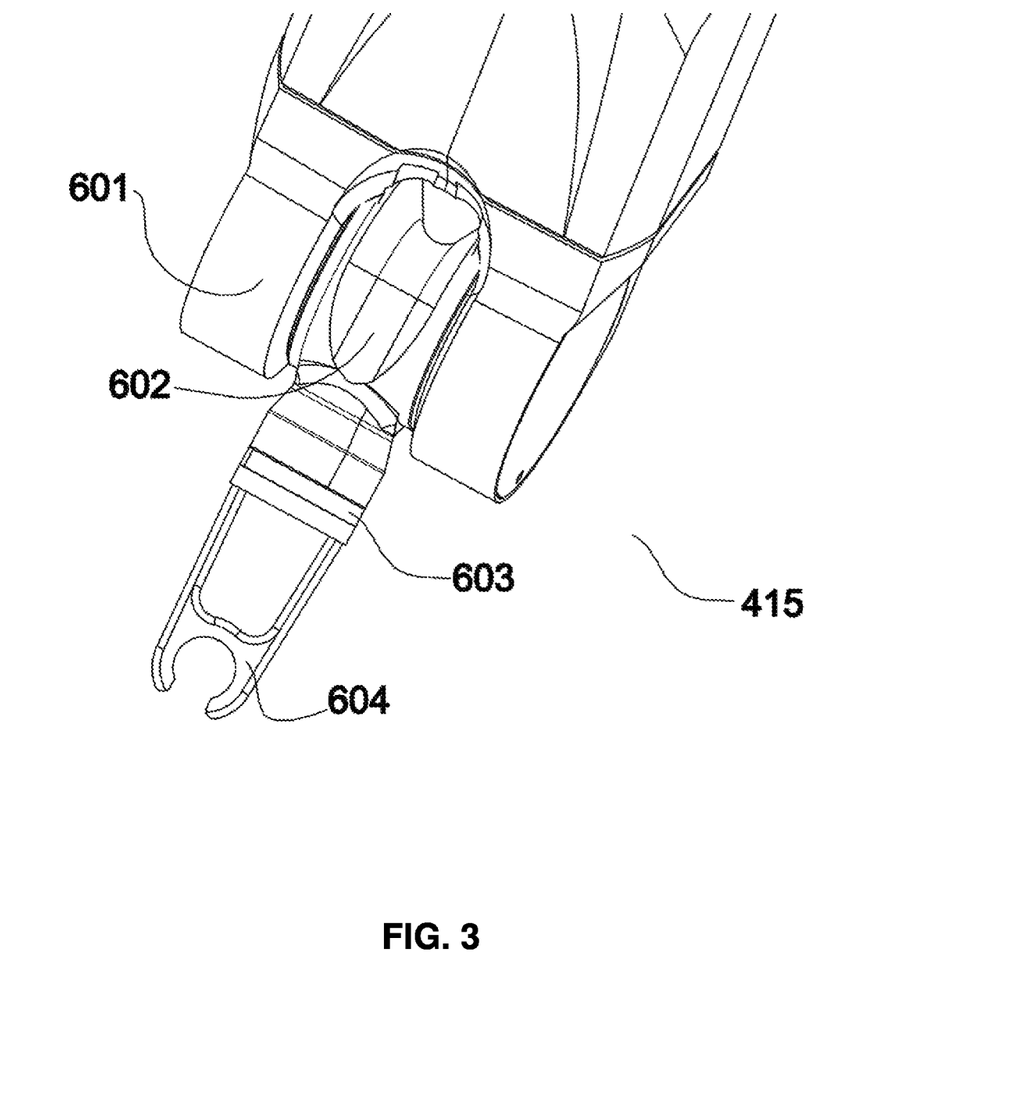
FIG. 3 shows detail of a robotic arm forming part of an apparatus for the protecting and unprotecting of a fluid path in a controlled environment enclosure

The mechanically unprotecting (304) the fill needle 414 when it is within controlled environment enclosure 420 can comprise using a robotic arm manipulation system 415 shown in FIG. 1. FIG. 3 illustrates part of the robotic arm manipulation system 415 of FIG. 1, wherein a forearm 601 is connected to a wrist 602, and the wrist 602 is connected to a tool flange 603. The end tool 604, shown in FIG. 3 as being fork shaped, has a partially opened bore of such diameter that the end tool 604 can slide around a narrow tubular section of needle hub 502 and the end tool 604 can move upwards to establish a precise locating fit to needle hub 502. For unprotecting (304) the fill needle 414 the end tool 604 moves the fill needle 414 with the fill needle sheath 503 and places the fill needle 414 with the fill needle sheath 503 in sheath removal station 413.

In one embodiment of the apparatus and method, the sheath removal station 413 heats the fill needle sheath 503, which thereby expands and releases its grip or seal to the needle hub 502. Practitioners in the field will appreciate that there are many different ways by which the fill needle sheath 503 can be removed from the fill needle 414. The end tool 604, through the motion of the robotic arm manipulation system 415, removes the fill needle 414 from the fill needle sheath 503. The fill needle sheath 503 can remain in the sheath removal station 413 while the robotic arm manipulation system 415 moves the fill needle 414 to the destination. In one embodiment of the apparatus and method the destination shown is the tray with vials 411 located on the pedestal 412 in FIG. 1.

The end tool 604 and the needle hub 502 can have various different other shapes allowing the use of various other closure systems such as, for example without limitation, a plug, a cap with sliding fit o-ring seal with minimal occluded surface area, a cap with membrane peel-off seal, or a twist-off cap. As understood by those skilled in the art, some closure systems will be more suitable than other closure system for use with particular sterilization methods.

Materials of lesser permeability can be used in the manufacture of the flexible tubing 405, but this is not always an option. Tubing permeability can also be reduced by adding additional layers to the tubing. Example methods for establishing such additional layers around the flexible tubing 405 include, but are not limited to, heat shrinking with non-permeable polymer such as PEP, multilayer coextrusion with non-permeable polymers, creating a diffusion barrier by polymeric coating such as poly(p-xylylene), encasing with layers of tape, and the fitting of a sleeve.

Figure 6:
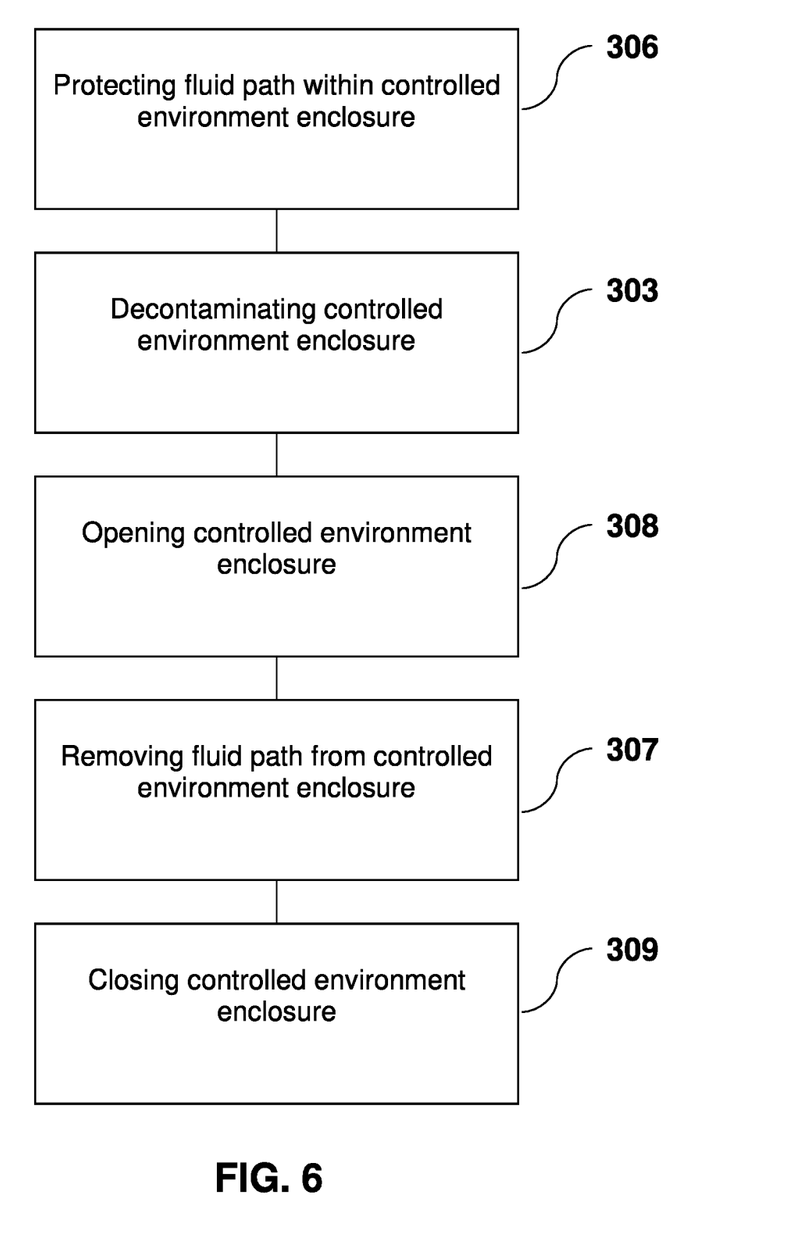
FIG. 6 shows a method flow chart of another aspect of the invention

In a further aspect of the invention there is provided a method for uninstalling a fluid path 404 from the controlled environment enclosure 420. Referring to the apparatus of FIG. 1 and the flow chart of FIG. 6. The method comprises mechanically protecting (306) the fluid path 404 within the controlled environment enclosure 420 once the use of fluid path 404 has been completed, decontaminating (303) the controlled environment enclosure 420, and removing (307) the fluid path 404 from the controlled environment enclosure 420. The mechanically protecting (306) the fill needle 414 can comprise using the robotic arm manipulation system 415 shown in FIG. 1.

The mechanically protecting (306) the fill needle 414 within controlled environment enclosure 420 can comprise using the robotic arm manipulation system 415 of FIG. 1. The end tool 604 (See FIG. 3) of robotic arm manipulation system 415 is used to move the fill needle 414 to and place it in the fill needle sheath 503, which is housed in the sheath removal station 413. The sheath removal station 413 heats the fill needle sheath 503 until the fill needle sheath 503 can slide over fill needle 414 to suitably seal to needle hub 502 after cooling, to thereby protect (306) the fill needle 414 within controlled environment enclosure 420. The robotic arm manipulation system 415 can then further move the protected fluid path 404 as may be required.

In a further aspect of the invention the mechanically unprotecting (304) and the mechanically protecting (306) the fill needle 414 using the robotic arm manipulation system 415 can be done automatically. For example, a suitable controller 440 (see FIG. 1), communicating control instruction with the controlled environment enclosure 420 via a control line 450, can be programmed to automatically unprotect (304) the fill needle 414 using the robotic arm manipulation system 415 once the decontaminating (303) the controlled environment enclosure 420 has been completed. Such automation obviates human intervention in the step of mechanically unprotecting (304) the fill needle 414. In an embodiment of the method, the step of decontaminating (303) the controlled environment enclosure 420 can also be managed by controller 440 This allows the remainder of the steps of installing the fill needle 414, beyond the step of introducing (302) the fluid path 404 into the controlled environment enclosure 420, to be automated using controller 440, including the use of the fill needle for the purpose for which it is installed, and the mechanically protecting (306) the fill needle 414 after such use.

Figure 7:
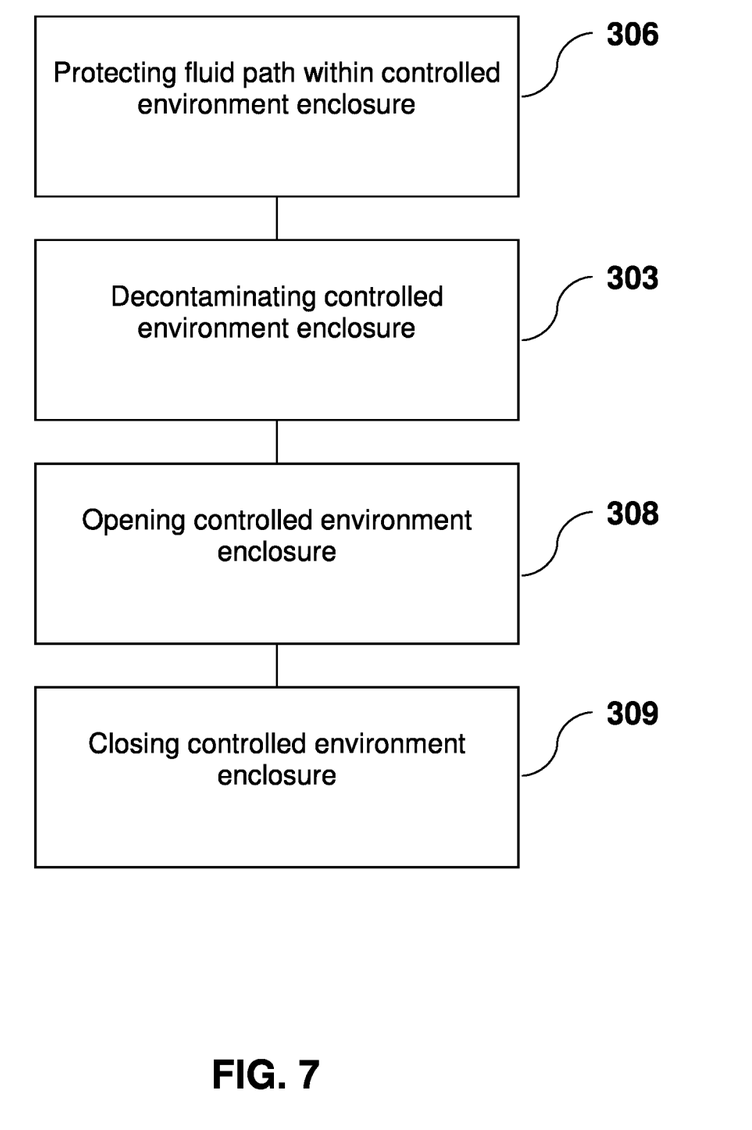
FIG. 7 shows a method flow chart of another aspect of the invention
Figure 8:
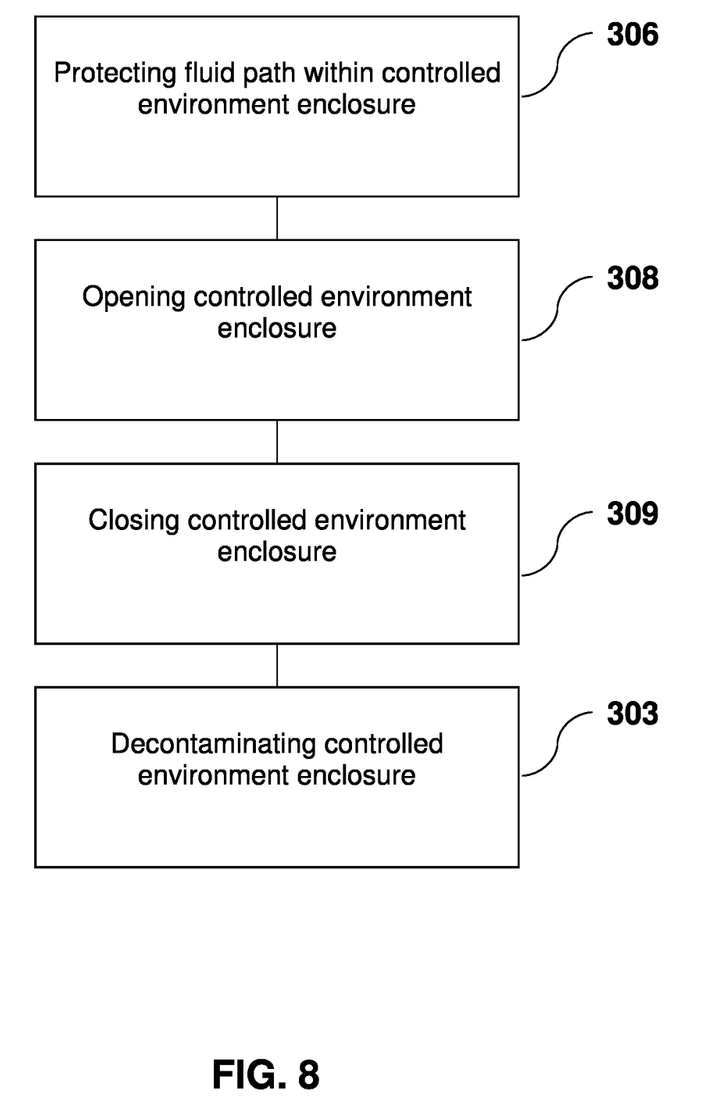
FIG. 8 shows a method flow chart of another aspect of the invention

In a further aspect of the invention there is provided a method for decontaminating the controlled environment enclosure 420 having a fluid path 404. The method comprises mechanically protecting (306) the fluid path 404 within the controlled environment enclosure by sealingly placing the fill needle sheath 503 over the fill needle 414 such that the fill needle sheath 503 seals with the needle hub 502; decontaminating (303) the controlled environment enclosure 420; and opening (308) and closing (309) the controlled environment enclosure 420. The opening (308) and closing (309) the controlled environment enclosure 420 can either be done after the decontaminating (303) the controlled environment enclosure 420, as may be the case when the fluid or the materials at the destination 411 are dangerous. This is shown in FIG. 7. Alternatively, the opening (308) and closing (309) the controlled environment enclosure 420 can either be done before the decontaminating (303) the controlled environment enclosure 420. This is shown in FIG. 8, as may be the case when the external environment holds potential of contaminating the fluid or the materials at the destination 411. The mechanically protecting (306) the fill needle 414 can comprise using the robotic arm manipulation system 415 shown in FIG. 1, as already described.

The protecting (306) the fill needle 414 using the robotic arm manipulation system 415 can be done automatically via controller 440 (see FIG. 14). Controller 440 can be programmed for automatically mechanically protecting (306) the fill needle 414 using the robotic arm manipulation system 415, prior to opening (308) and closing (309) the controlled environment enclosure 420. The opening (308) and closing (309) the controlled environment enclosure 420 can likewise be automated via controller 440.

Additional Notes

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a tangible computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

The invention claimed is:

1. An apparatus for protection and unprotection of a pharmaceutical dispensing fluid path within a controlled environment enclosure requiring apparati structured and arranged for aseptic processing, comprising:
   a fluid path extending from a pharmaceutical source end to a pharmaceutical dispensing end, the fluid path dispensing end terminated by a fill needle with removable sheath;
   a remotely operated manipulation system for protection and/or unprotection of the fluid path; and
   a removal station that includes a surface operative to interact with part of the sheath.

2. The apparatus of claim 1 wherein the remotely operated manipulation system includes a robotic arm manipulation system.

3. The apparatus of claim 1 wherein the remotely operated manipulation system includes a robot end tool including at least one surface that is shaped to hold the fill needle.

4. The apparatus of claim 1 wherein the fluid path is a pre-sterilized unit.

5. The apparatus of claim 1 wherein the fluid path comprises a filter.

6. The apparatus of claim 5 wherein the filter is a sterile filter.

7. The apparatus of claim 1 wherein the fluid path is configured and arranged to convey an aseptic fluid.

8. The apparatus of claim 1 wherein the fluid path includes flexible tubing.

9. The apparatus of claim 1 wherein the fluid path includes means for transferring a fluid.

10. The apparatus of claim 9 wherein the means for transferring a fluid includes a pump.

11. The apparatus of claim 10 wherein the pump is a peristaltic pump.

12. The apparatus of claim 9 wherein the means for transferring a fluid includes a fluid container.

13. The apparatus of claim 1 wherein the fill needle includes a needle hub circumferentially disposed about the fill needle.

14. The apparatus of claim 13 wherein the sheath is comprised of material having a different thermal expansion coefficient than the needle hub.

15. The apparatus of claim 14 wherein the removal station includes means for heating the sheath.

16. The apparatus of claim 1 wherein the sheath is comprised of material capable of having a sliding fit on the fill needle.

17. The apparatus of claim 14 wherein the material of the sheath is one of porous PTFE and steam permeable elastomeric material.

18. The apparatus of claim 2 wherein the remotely operated manipulation system further comprises a controller for communicating control instructions to the robotic arm manipulation system.

19. The apparatus of claim 1 wherein a portion of the fluid path is disposed outside the controlled environment enclosure.

20. An apparatus for protection and unprotection of a fluid path in a pharmaceutical fluid dispensing system, comprising:
   a controlled environment enclosure;
   a fluid path disposed within the controlled environment enclosure, the fluid path extending from a pharmaceutical source end to a pharmaceutical dispensing end, the dispensing end terminated by a fill needle with removable sheath;
   a remotely operated manipulation system for protection and/or unprotection of the fluid path; and
   a removal station disposed within the controlled environment enclosure, the removal station including a surface operative to interact with part of the sheath.

21. The apparatus of claim 20 wherein the remotely operated manipulation system includes a robotic arm manipulation system.

22. The apparatus of claim 20 wherein the remotely operated manipulation system includes a robot end tool including at least one surface that is shaped to hold the fill needle.

23. The apparatus of claim 20 wherein the fluid path is a pre-sterilized unit.

24. The apparatus of claim 20 wherein the fluid path comprises a filter.

25. The apparatus of claim 24 wherein the filter is a sterile filter.

26. The apparatus of claim 20 wherein the fluid path is configured and arranged to convey an aseptic fluid.

27. The apparatus of claim 20 wherein the fluid path includes flexible tubing.

28. The apparatus of claim 20 wherein the fluid path includes means for transferring a fluid.

29. The apparatus of claim 28 wherein the means for transferring a fluid includes a pump.

30. The apparatus of claim 29 wherein the pump is a peristaltic pump.

31. The apparatus of claim 28 wherein the means for transferring a fluid includes a fluid container.

32. The apparatus of claim 20 wherein the fill needle includes a needle hub circumferentially disposed about the fill needle.

33. The apparatus of claim 32 wherein the sheath is comprised of material having a different thermal expansion coefficient than the needle hub.

34. The apparatus of claim 33 wherein the removal station includes means for heating the sheath.

35. The apparatus of claim 20 wherein the sheath is comprised of material capable of having a sliding fit on the fill needle.

36. The apparatus of claim 35 wherein the material of the sheath is one of porous PTFE and steam permeable elastomeric material.

37. The apparatus of claim 21 wherein the remotely operated manipulation system further comprises a controller for communicating control instructions to the robotic arm manipulation system.

38. The apparatus of claim 20 wherein a portion of the fluid path is disposed outside the controlled environment enclosure.

* * * * *